(12) United States Patent
Coates

(10) Patent No.: US 6,926,705 B1
(45) Date of Patent: Aug. 9, 2005

(54) PROTECTIVE UNDERGARMENTS HAVING ANCHORED POCKETED-SLING STRUCTURES AND MANUFACTURING METHOD THEREFOR

(75) Inventor: Fredrica V. Coates, Winston-Salem, NC (US)

(73) Assignee: Tailored Technologies, Inc., Winston-Salem, NC (US)

( * ) Notice: Subject to any disclaimer, the term of this patent is extended or adjusted under 35 U.S.C. 154(b) by 0 days.

(21) Appl. No.: 09/512,085

(22) Filed: Feb. 24, 2000

Related U.S. Application Data (60) Provisional application No. 60/121,960, filed on Feb. 25, 1999.

(51) Int. Cl.[7] .............................................. A61F 13/20
(52) U.S. Cl. ........................... 604/385.19; 604/385.14; 604/398; 604/401
(58) Field of Search ...................... 607/385.01, 385.03, 607/385.14, 385.15, 385.19, 385.24–385.3, 607/386, 387, 391, 393–402

(56) References Cited

U.S. PATENT DOCUMENTS

| | | | | |
|---|---|---|---|---|
| 1,977,604 A | * | 10/1934 | Alsop ........................ 604/401 |
| 2,016,355 A | * | 10/1935 | Alsop ........................ 604/396 |
| 2,493,492 A | | 1/1950 | Malamut | |
| 2,532,029 A | * | 11/1950 | Medoff ...................... 604/394 |
| 2,545,216 A | | 3/1951 | Toussie | |
| 2,545,674 A | * | 3/1951 | Ralph ........................ 604/397 |
| 2,691,983 A | * | 10/1954 | Bernard ...................... 604/397 |
| 2,893,393 A | * | 7/1959 | Pressley ..................... 604/397 |
| 2,977,957 A | * | 4/1961 | Clyne ........................ 604/396 |
| 3,143,112 A | * | 8/1964 | Sanford ...................... 604/397 |
| 4,664,663 A | * | 5/1987 | Brier ......................... 604/397 |
| 4,898,594 A | * | 2/1990 | Cottenden ................... 604/397 |
| 5,137,526 A | | 8/1992 | Coates | |
| 5,360,422 A | * | 11/1994 | Brownlee et al. ...... 604/385.14 |
| 5,409,476 A | | 4/1995 | Coates | |
| 5,722,127 A | | 3/1998 | Coates | |
| 6,248,098 B1 | * | 6/2001 | Sayama ................. 604/385.28 |
| 6,383,170 B1 | * | 5/2002 | Mishima et al. ....... 604/385.19 |
| 6,443,933 B1 | * | 9/2002 | Suzuki et al. .......... 604/385.04 |
| 6,527,756 B1 | * | 3/2003 | Mishima et al. ....... 604/385.19 |

FOREIGN PATENT DOCUMENTS

| | | | | |
|---|---|---|---|---|
| CH | 577281 | * | 7/1976 | ................. 604/398 |
| FR | 549579 | * | 2/1923 | ................. 604/399 |
| GB | 849573 | * | 9/1960 | ................. 604/398 |

* cited by examiner

*Primary Examiner*—Karin Reichle
(74) *Attorney, Agent, or Firm*—McDermott Will & Emery LLP (57) ABSTRACT

A reusable infant or adult diaper with an inner anchored pocketed sling structure adjoining an outer shell or pant-type garment. The outer shell or garment fits the wearer's torso and legs, and the inner anchored sling fits and conforms to the wearer's pubic region. Included are mechanisms to fasten and remove the anchored sling from underwear and to stabilize and/or anchor the sling when retrofitted to conventional underwear.

8 Claims, 14 Drawing Sheets

PROTECTIVE UNDERGARMENTS HAVING ANCHORED POCKETED-SLING STRUCTURES AND MANUFACTURING METHOD THEREFOR

RELATED APPLICATIONS

The present application claims the benefit of U.S. Provisional Application Ser. No. 60/121,960, entitled "PROTECTIVE UNDERGARMENTS HAVING ANCHORED POCKETED-SLING STRUCTURES AND MANUFACTURING METHOD THEREFOR", filed on Feb. 25, 1999, whose contents are incorporated by reference.

FIELD OF THE INVENTION

This invention relates generally to protective undergarments, and more particularly to reusable underwear having, or retrofitted with, novel body fluid containment and fecal matter collection structures.

BACKGROUND OF THE INVENTION

To enhance the fluid and fecal containment properties of protective underwear, U.S. Pat. Nos. 5,137,526 and 5,409,476, issued to Fredrica Coates, describe protective underwear having a waterproof or water-resistant sling with its front and rear ends adjoined through connecting pieces to an outer shell. This sling isolates body fluids from spreading to the outer region of the shell by implementing elastic on the outer perimeter edge of the sling or waterproof gussets mounted on opposite sides of the sling. The elasticized and gusseted sling design is effective, although the volume of fluid able to be contained in this structure is limited.

As an improvement, in U.S. Pat. No. 5,722,127, issued to Fredrica Coates, the sling is enhanced to form a deeper pocket and fasteners of greater adjustability are provided to retain the garment to the wearer. However, even with improved fit and a deeper inner pocketed sling, there still remains a need for a greater circumferential area for fluid and fecal matter containment. Hence, further disclosed in the '127 patent is a pocketed sling for retaining fluid absorbent pads. Coates application Ser. No. 08/792,735, filed on Jan. 31, 1997, now U.S. Pat. No. 6,254,583, discloses a frontal hidden pocket added to a connecting frontal piece for enhanced circumferential area and hence fluid absorption. However, a need continues to exist for an alternative device for increasing circumferential area for fluid containment. It is also preferred to provide body fluid containment structures, within what will appear to be conventional underwear, which is particularly desirable for an adult wearer.

There continues to exist a need for more effective protective underwear, and garments for bed wetters or adults, that provide containment while preserving underwear of aesthetic appeal. Prior devices, sewn or heat sealed to garments, are uncomfortable or tend to leak at places in the garment where holes are formed by sewing needles used during assembly.

SUMMARY

A protective garment comprises an outer layer of fluid-resistant material shaped to conform to a buttock and leg region of a user, an anchor layer secured to the outer layer and having a shape conforming to that of the outer layer, and an inner layer of fluid-resistant material with all sides thereof attached to the anchor layer. The attached sides of the inner layer are displaced from corresponding sides of the anchor layer, and the inner layer extends outwardly from the anchor layer to form a pocket.

Another embodiment of protective garment comprises a first, outer layer of fluid-resistant material, a second layer of material having its peripheral edge attached to the first layer, the second layer conforming in shape to that of the first layer and having a central opening, and a third layer of material attached only at its outer edge by an elastic strip to the second layer and extending beneath the opening toward to first layer, the third layer being proportioned relative to the opening so as to form a pocket, the entire periphery of which is beneath the second layer and larger than the opening.

BEST MODE FOR CARRYING OUT THE INVENTION

Figure 1:
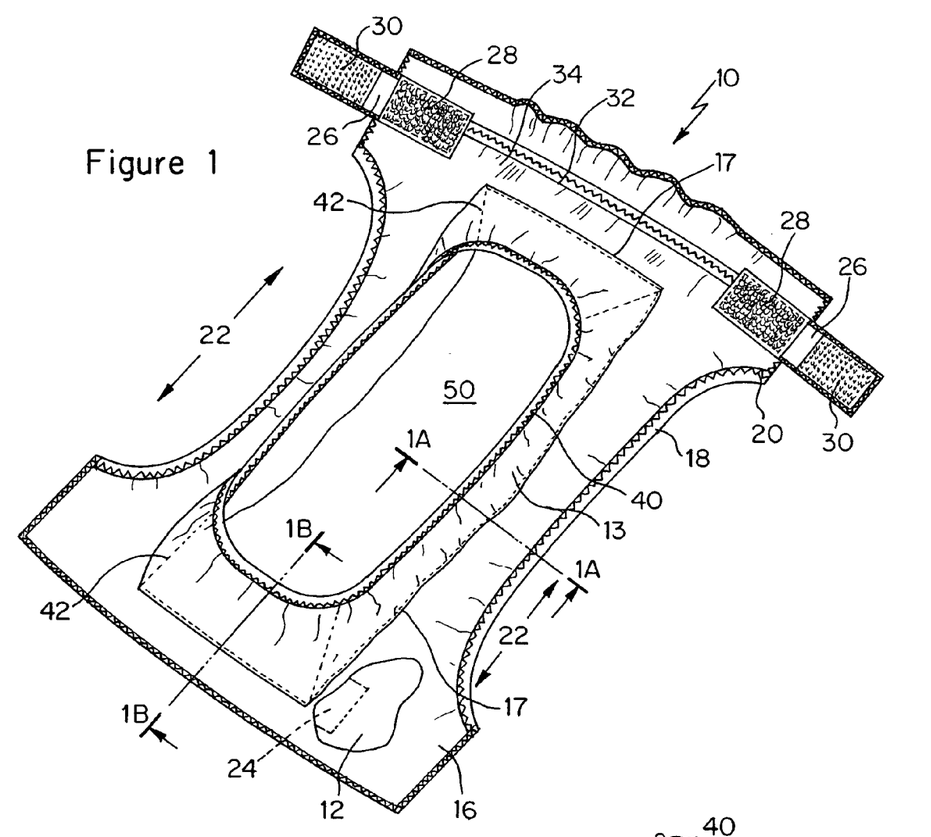
FIG. 1 is a perspective view showing one embodiment of a reusable diaper with anchored pocketed sling, produced in accordance with the principles of the invention and shown open into position to be worn, with cutaway to expose an underlying shell.
Figure 1A:
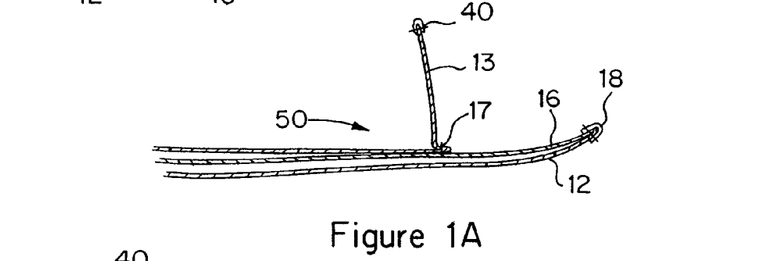
FIG. 1A is a cross-sectional view of a diaper with anchored sling, taken along the line 1A—1A in FIG. 1.

Referring to FIGS. 1A–1H, a reusable diaper in accordance with one embodiment of the invention, designated generally by numeral 10, comprises a waterproof or water-resistant (breathable type fabric) diaper shell (outer shell) 12 within which is retained a fluid containment pocket 50, positioned to be located about the groin when worn by an infant or adult. Referring to FIG. 1A, the diaper is formed of three layers; a waterproof or water-resistant outer shell 12, an inner liner 16 generally soft to the touch and optionally of fluid absorbent fabric, and a layer forming a fluid containment pocket, or anchored pocketed-sling, 50, of water-resistant or waterproof material 13. The two outer layers 12 and 16 of the diaper are generally of the same shape, and the anchor cloth 16 is on the inside of, and aligned with, the outer shell 12. This liner 16 forms an attachment mechanism at a stitch line 17 to anchor the pocketed sling 50 to shell 12. The outer shell 12 and its inner liner 16 are joined at the leg hole by a leg elastic strip 18, which convolutes the two layers, stitched at line 20 and holds the two layers together to form a leg hole 22. The inner pocketed sling is positioned and attached (stitched) centrally to the inner liner 16 only. Hence, the stitching does not pierce shell 12.

Shell 12 has a fastener 24 of loop-type filamentary material attached to the outer frontal surface of diaper 10. In the rear portion of the outer corners of diaper 10 are fasteners 26, affixed to the diaper 10 such that hook-type filamentary material 30 closes onto loop material 28 to protect the hook material from accumulating lint during laundering, with the hook and loop materials being separated from each other by a space to form a hinge. The elastic strip 32 conforms the layers to fit the waist and buttocks region of the wearer through gathers 34.

Seam line 42, which may be replaced by heat sealing, assembles the corners of the pocket. This assembly may also be accomplished by folding the corners 21 inward to the reverse side, and then stitching or sealing to establish an inside seam.

Referring to FIG. 1A, which is a cross-sectional view of outer layer 12 connected to the inner layer 16 at elastic strip 18, stitch line 17 adjoins pocket 50 to the inner liner 16. Elastic trim 40 forms an adjustable pocket opening to receive fluid into a fluid absorbing pad (not shown). Stitch line 42 connects the corners of the pocket 50, as previously described, and the pocket is bounded by elastic strip 40 to present a smooth finished surface to contact the wearer.

Figure 1B:
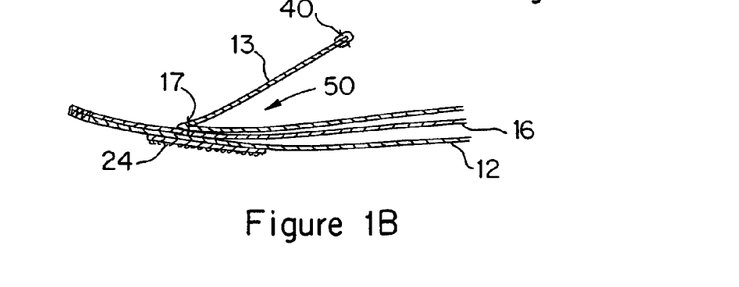
FIG. 1B is a cross-sectional view of a diaper with anchored sling taken along line 1B—1B in FIG. 1.

FIG. 1B is similar to FIG. 1A, but depicts the presence of loop-type filamentary material 24 positioned on the outer surface of shell 12. The loop material 24 fastens the garment to the wearer when hook tabs 30, shown in FIG. 1, close onto the front of the garment.

Figure 1C:
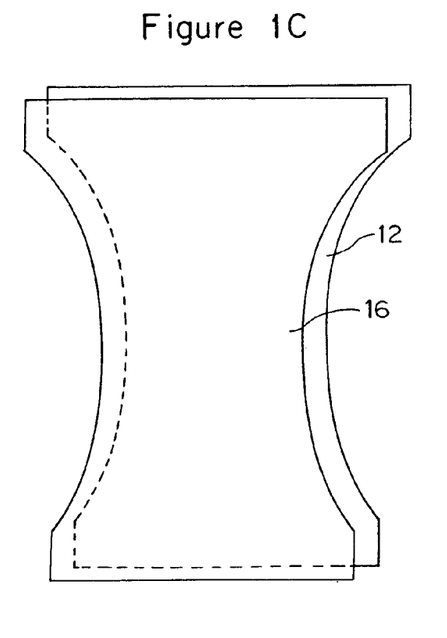
FIG. 1C shows the anchor cloth overlying the outer shell, as a first step in manufacture of the reusable diaper.
Figure 1D:
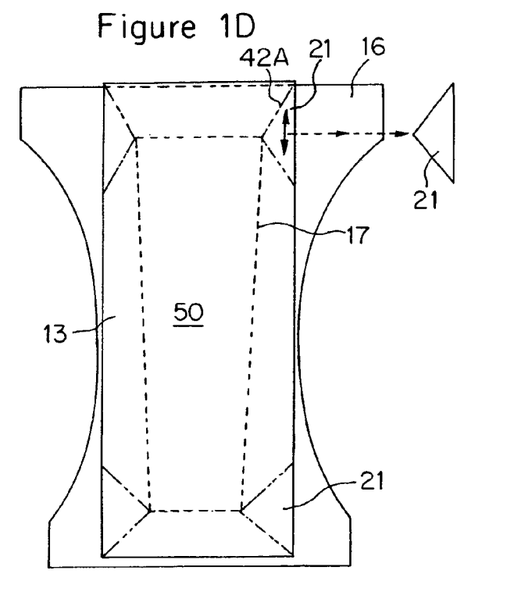
FIG. 1D shows the anchor cloth with a mounted pocket sling, together with cutting away of the corner of the pocketed sling.

FIGS. 1C–1H show the construction method by which three layers of fabric come together to form a leak proof undergarment interior. In FIG. 1C, a piece of anchor cloth 16 is positioned over outer shell 12, similarly configured as a first step in the manufacture of anchored pocket 50. In FIG. 1D, stitch line 17 pierces the cloth 16 in a rectangular pattern and attaches to hold pocket 50 to its anchor cloth now stitched centrally. The edges or sides of the material 13 take shape into a pocket-shape 50 as corners 21 are removed, and the sides become seamed at edge 42A by seam line 42, FIG. 1. The pocket may alternatively take shape by folding the corners 21 at what would be seam edges 42A, and then seaming, i.e. the corners 21 are not removed.

Figure 1E:
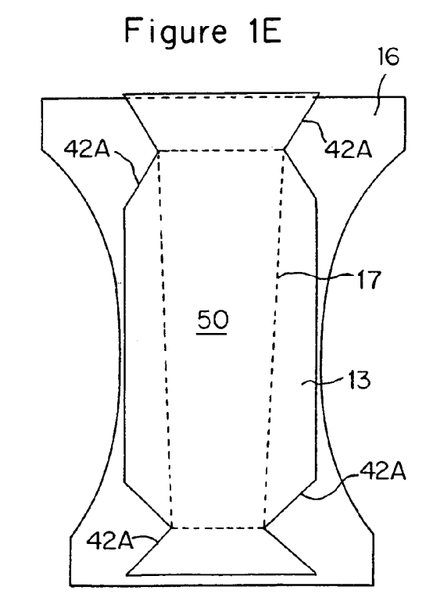
FIG. 1E is a view of the pocketed sling, with the four corners of the pocket removed.
Figure 1F:
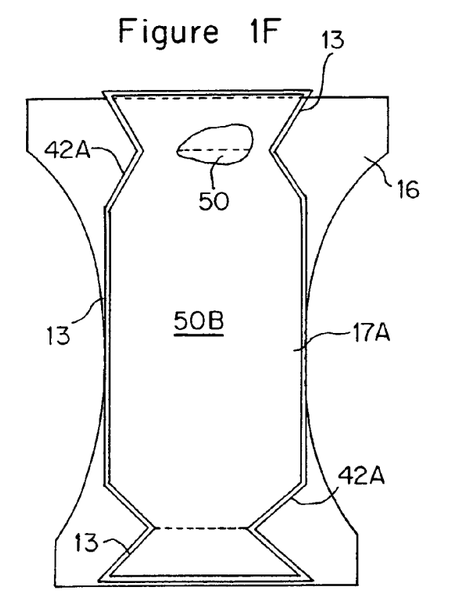
FIG. 1F shows a double pocketed sling, where a second pocket is formed and anchored by a first anchored pocket.

In FIG. 1E, bulk is advantageously reduced in the garment by removing the triangular corners 21 shown in FIG. 1D. In FIG. 1F, an additional piece of fabric at 50B is optionally added at stitch line 17A (for either waterproof or absorbing purpose) at pocket 50 as it overlays the seam line 17 of the primary pocket 50.

Figure 1G:
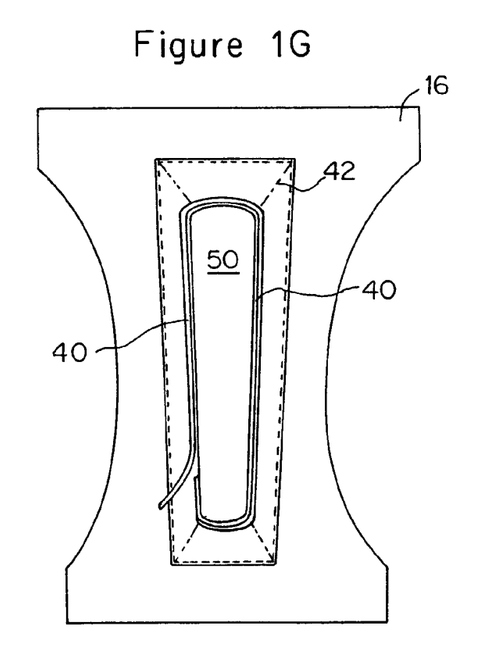
FIG. 1G shows the four corners of the pocketed sling joined and formed with a pocket edge covered by an elastic.

In FIG. 1G, pocket 50 is now formed as seamed, joined or heat sealed at 42, so as to keep the pocket sides properly shaped, and with elastic 40 convoluting the edge of the pocket.

Figure 1H:
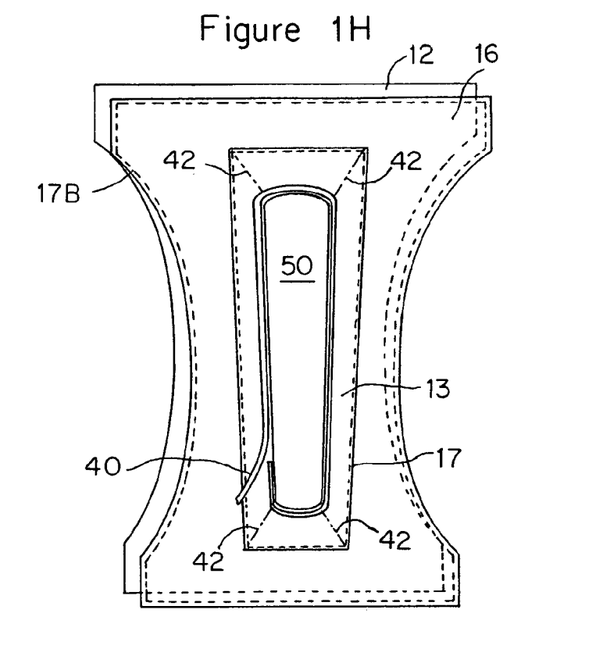
FIG. 1H shows assembly of an anchored pocketed sling to the anchor cloth overlying a shell.

In FIG. 1H, the three layers are now in position to be joined at stitch line 17B. The layers are held together for assembly of the garment to its fasteners and leg hole elastic strips, as seen in FIGS. 1, 1A and 1B.

Figure 2:
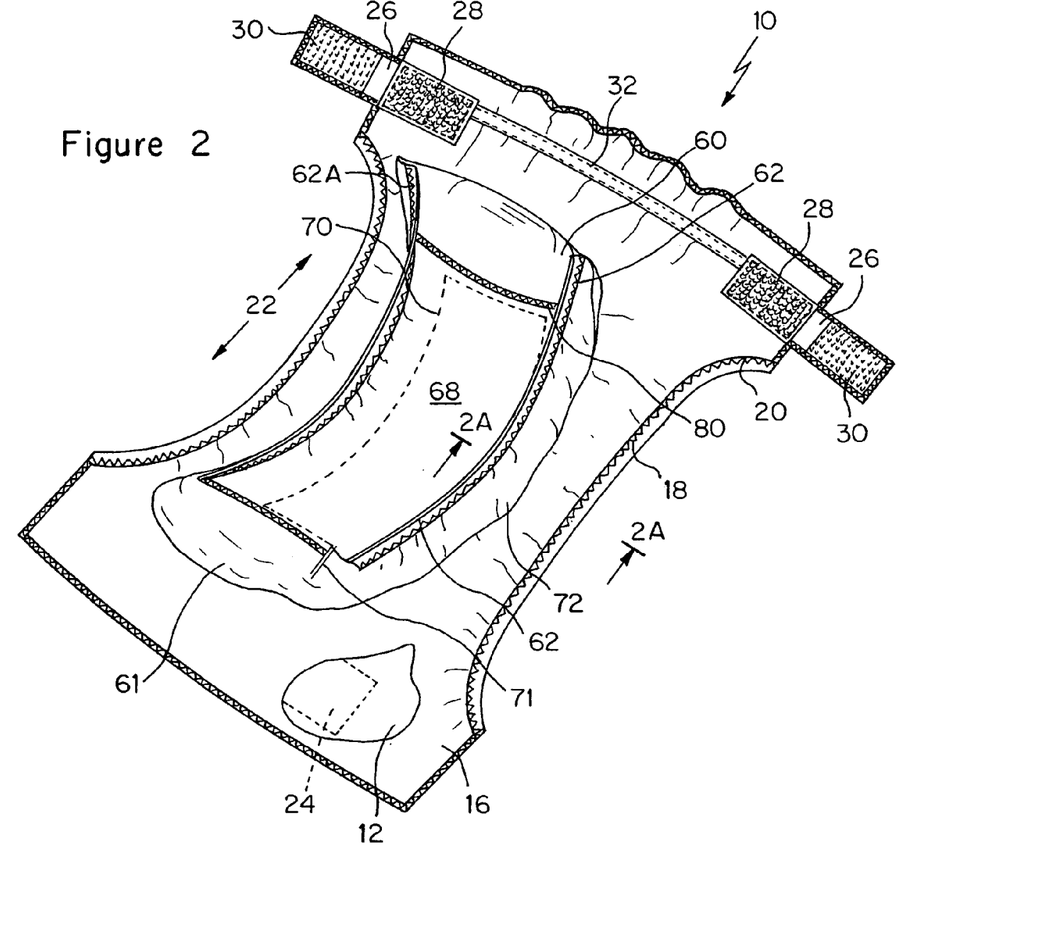
FIG. 2 is a perspective view showing another embodiment of the invention with anchor pocket sling having extended cuffed pockets, with cutaway to expose underlying shell.

Refer now to FIG. 2, depicting another embodiment of the invention, in which the outer shell is the same, but sling configuration different compared to the embodiment of FIG. 1. In FIG. 2, diaper 10 is again composed of three layers; outer layer 12 of water-resistant material, inner layer 16 that is not water-resistant and an inner fabric 72 cuffed to form pocketed sling 68 of water-resistant material. The fabric 72 at the ends of the rectangular pocketed sling are folded to form cuffs 60 and 61, the rear end cuff 60 being formed by folding outer perimeter edge 80 of fabric 72 inward, and the two raw edges of the fold inserted into elastic strip 62. Elastic strip 62 extends longitudinally to frontal cuff 61, where a frontal pocket is formed from the cuff 61 as the raw edges 61B and 71A are joined. Cuff pocket 60 is formed in the rear portion of the diaper by adjoining folded edges within the elastic, as compared to frontal cuff pocket 61 where elastic 62 covers edges 61B and 71A, which edges are joined at seam line 71 on the interior side of the formed cuff pocket. Optionally, the elastic may be omitted on underside at 71 as finished edge is formed by seam line 71 rather than elastic 62. The rear cuff outer corner may be stitched down at stitch line 62A. The entire pocketed-sling 68 is attached to anchor cloth 16 in the central portion of diaper 10 at stitch line 70, which forms a stabilizing rectangular attachment of cuffed pocketed-sling 68 to its anchor cloth 16. Leg hole 22 and fasteners 24 and 26 are identical to those depicted in FIG. 1.

Figure 2A:
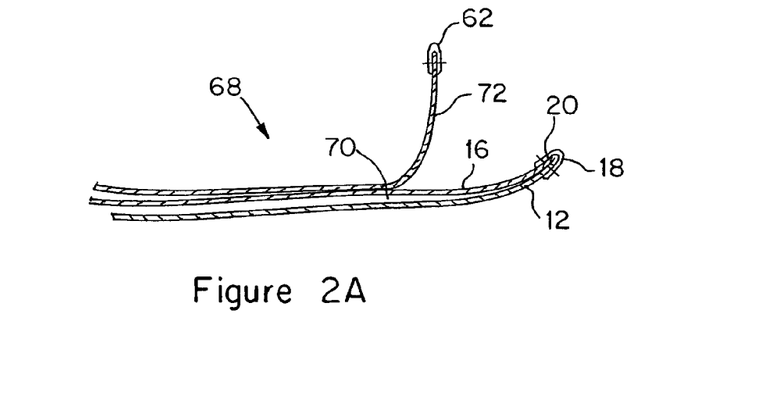
FIG. 2A is a cross-sectional view of the diaper of FIG. 2, with anchored pocketed-sling and extending cuff pockets, taken along line 2A—2A in FIG. 2.

Referring to FIG. 2A, which is a cross-sectional view of pocket 68, outer layer 12 is connected to inner layer 16 at elastic trim 18, and held fast by zig-zag or straight stitching at 20. Fabric sidewall 72 is terminated at strip 62. As depicted in FIG. 2, pocket 60 is formed as the sidewall of fabric 72 of pocket 68 bends along stitch line 70.

Figure 2B:
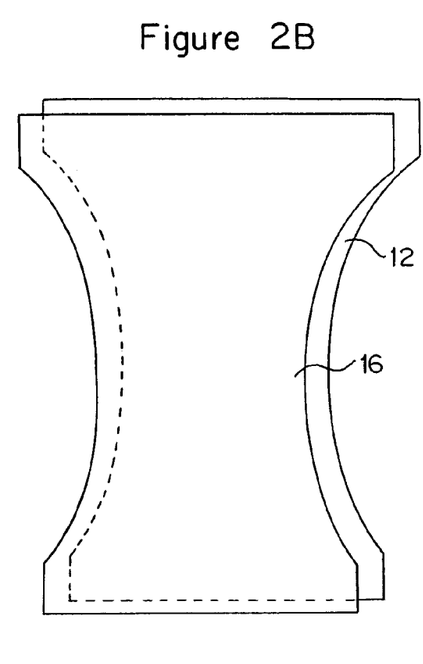
FIG. 2B is a plan view of the anchor cloth overlying the shell cloth.
Figure 2C:
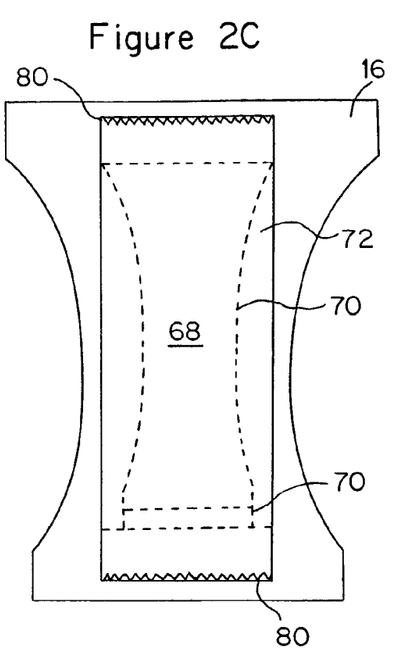
FIG. 2C shows the anchor cloth with a mounted fabric piece to form a cuffed pocketed sling.

Manufacture is carried out first by overlaying cloth 16 on waterproof cloth 12 as its liner, as shown in FIG. 2B. In FIG. 2C, liner 16 and fabric piece 72 are stitched in an hourglass fashion at 70 to anchor cloth 16. Opposite ends of waterproof fabric piece 72 are overlock stitched at 80.

Figure 2D:
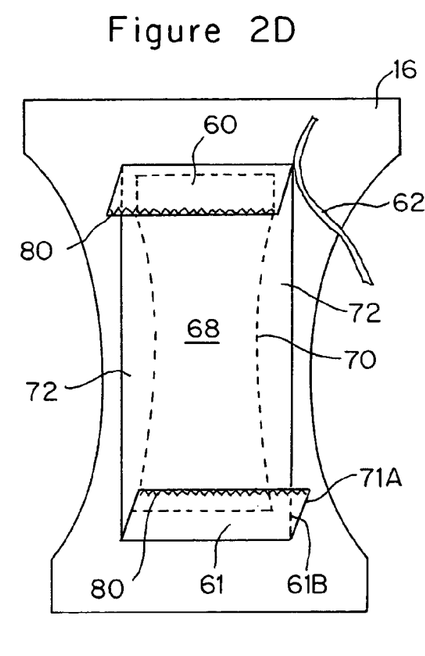
FIG. 2D shows mounting and folding of the cuffed pocketed sling on its anchor cloth.

FIG. 2D shows the opposite ends being folded inward to form cuff 60 and folded backward forming cuff 61. At cuff 60, the folded sides will meet and be encased in elastic strip 62, bending the wall of fabric 72 inward. The opposite end of the cuff is formed in a different fashion, as end 80 of cuff 61 is folded backward, and the two raw edges 61B and 71A are encased in elastic strip 62.

Figure 2E:
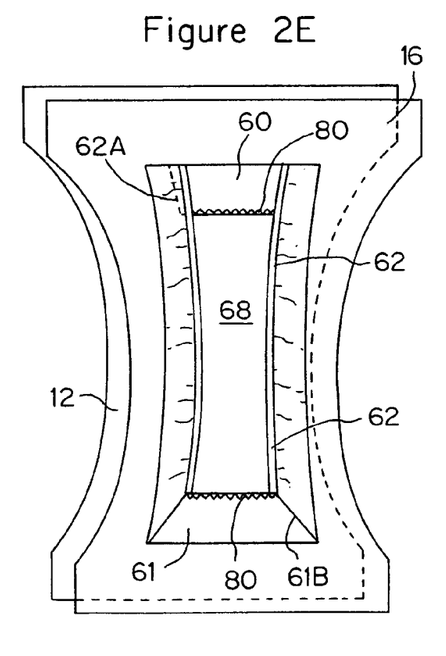
FIG. 2E shows assembly of a cuffed pocketed sling to the anchor cloth and shell.

In FIG. 2E, the cuff is reversed and seam 71 is made flush with the fabric raw edges, and elastic is now on the inside of pocket 68. Optionally, a tacking 62A can be added to hold elastic down at cuff 60. The formed pocket 68 adjoined to cloth 16, overlies outer shell fabric 12, and is ready for assembly as a garment of protective underwear.

Figures 3, 3A, 3B:
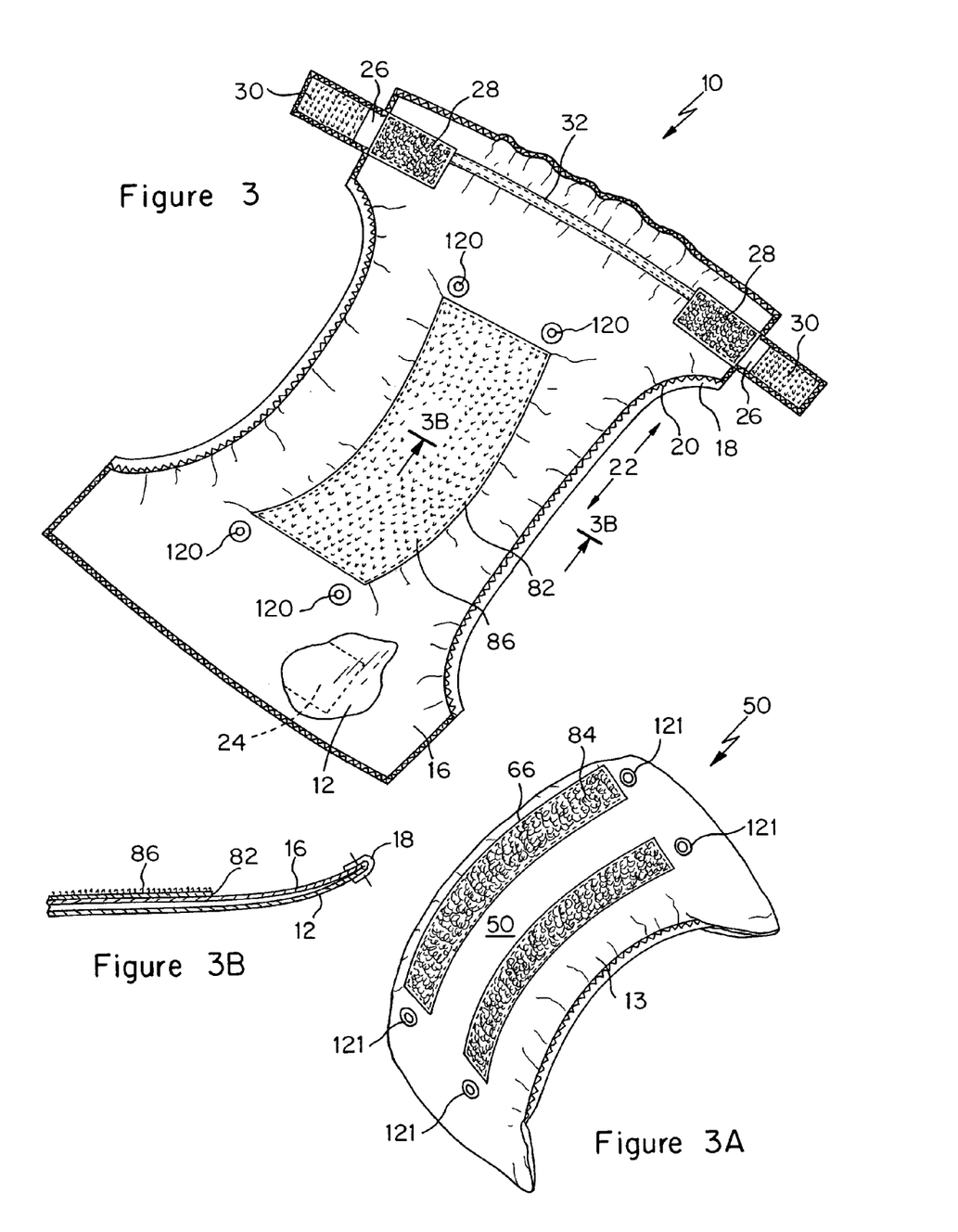
FIG. 3 shows another embodiment of the invention, with fasteners for anchoring a pocketed sling, produced in accordance with the invention, with cutaway to expose underlying shell.
FIG. 3A shows a removable pocketed sling with an attachment mechanism at the reverse side of the sling.
FIG. 3B is a cross-sectional view of the sling taken along line 3B—3B in FIG. 3.

In another embodiment of the invention, depicted in FIG. 3, diaper 10 is composed of two layers, with liner 16 and shell 12 connected at elastic strip 18 by stitching 20. The absorbing pocketed-sling 50 of FIG. 1 is detachable through an optional fastener material, such as Velcro® in the form of a rectangular sewn piece 86 sewn at stitch line 82, and/or as snaps 120. In FIG. 3B, the Velcro® fastener is mounted at line 82 on anchor cloth 16; in FIG. 3A, the pocketed sling 50 is shown detached from its anchor cloth to expose the underlying attachment of Velcro® strips 84 attached to the sling at stitching 66, and/or snaps 121.

Figure 3C:
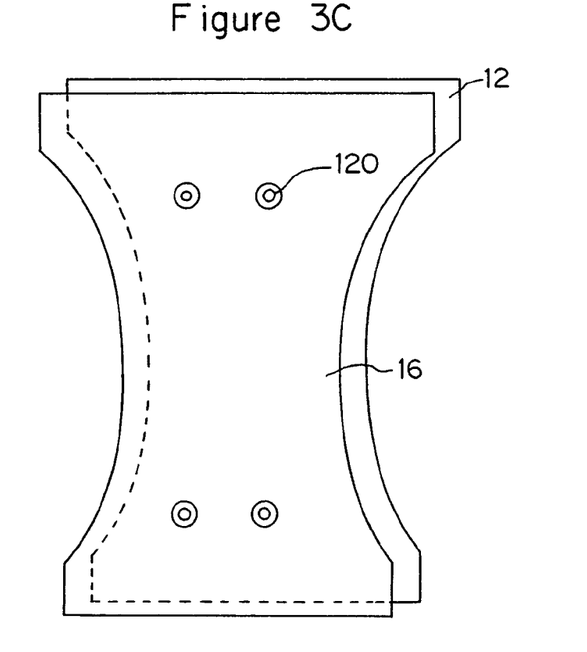
FIG. 3C shows the anchor cloth with a snap attachment for the pocketed sling structure.
Figure 3D:
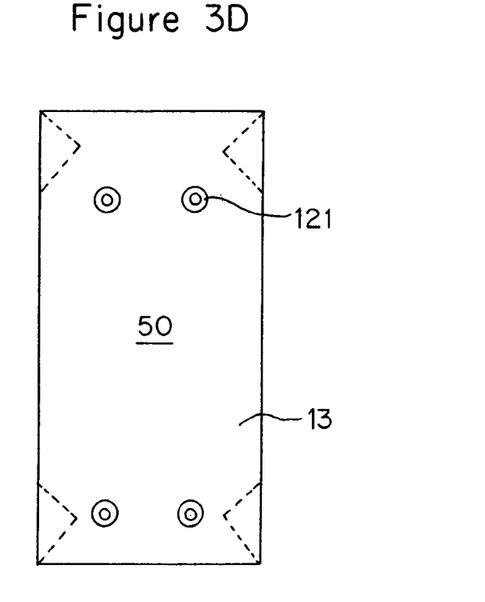
FIG. 3D shows a pocketed sling cloth with corresponding snap attachment mechanism.
Figure 3E:
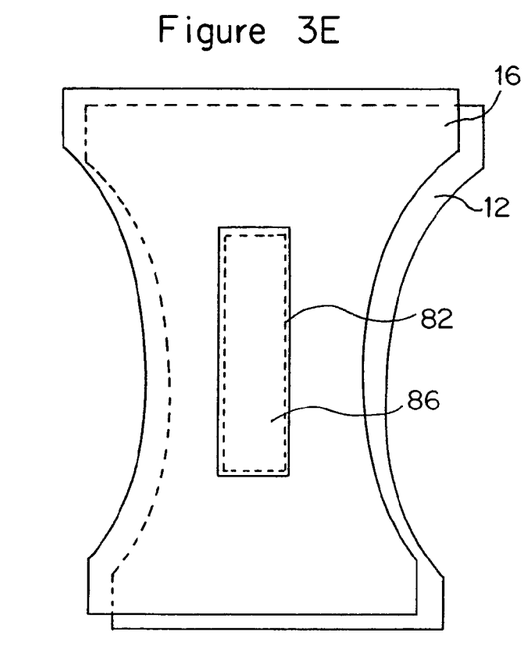
FIG. 3E is a view of the anchor cloth having a Velcro® fastening attachment mechanism.
Figure 3F:
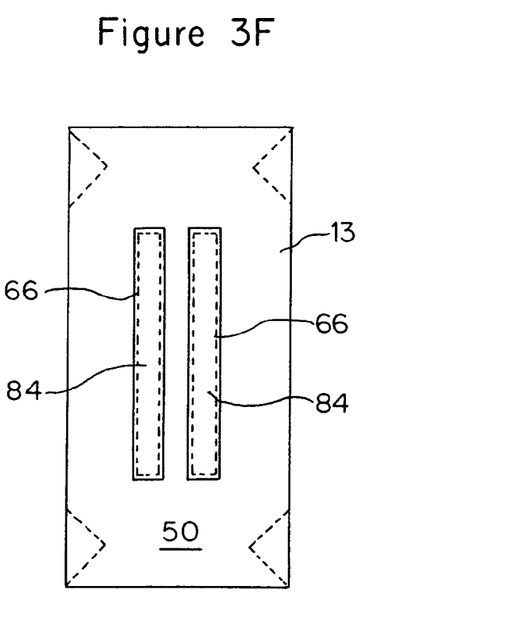
FIG. 3F shows the pocketed sling cloth with corresponding Velcro® attachment tabs.

FIGS. 3C–3F show optional placement of the fastening means for enabling the pocketed sling to be detached from its anchor cloth. FIG. 3C shows the mounting of four male snaps 120 overlying shell 12, FIG. 3D shows the pocket piece 50 with corresponding female snaps 121, FIG. 3E shows Velcro® loop material mounted on anchor cloth 16 overlying cloth 12, and FIG. 3F shows a pocket 50 formed with hook fastener strip 84 stitched at 66 to be coupled with a rectangular member 86 when the pocket is fully formed, as shown in FIG. 1.

Figure 4:
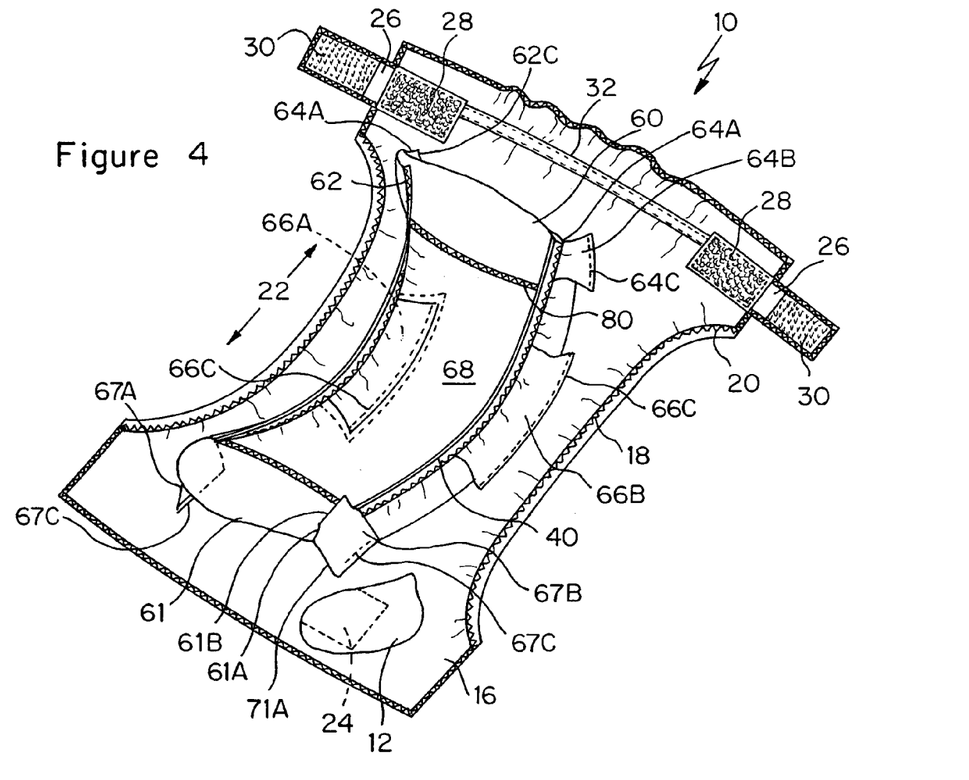
FIG. 4 shows another embodiment of an anchored sling and strip anchors, produced in accordance with the invention, with cutaway to expose an underlying shell.
Figure 4A:
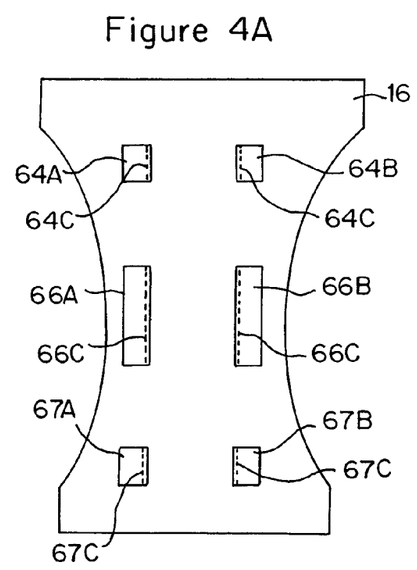
FIG. 4A shows the anchor cloth with attached strips in position to hold the pocket.
Figure 4B:
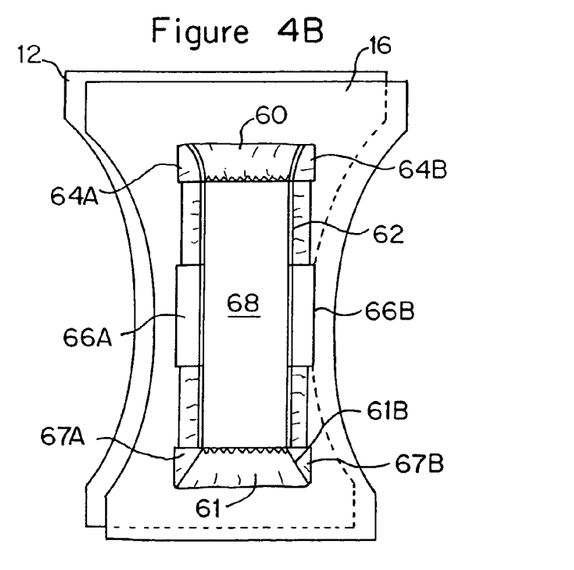
FIG. 4B shows a mounted pocket sling, held by anchor strips on an anchor cloth and overlying shell cloth.

In another embodiment, depicted in FIG. 4, diaper 10 is composed of two layers of fabric: an inner layer overlying a shell 12. A pocketed sling device similar but not identical to the types shown in FIGS. 1-3, is now anchored to the liner cloth 16 with strips of fabric 64A, 66A, 67A, positioned on one side of the anchor cloth 16, and on the opposite side anchor strips 64B, 66B and 67B are positioned to hold and stabilize the pocket. In this figure, the anchor strips are each tacked to the anchor cloth 16; 64A is tacked at 62C, 66A at 66C, 67A at 67C, 64B at 64C, 66B at 66C and 67B at 67C. As the first step in the stabilization of pocketed sling 68, FIG. 4A shows the tacking on the anchor cloth 16, and in FIG. 4B the strips each bend inward into the elastic strip 62 as the pocket is formed. Just as in FIG. 2, elastic strip 62 is exposed at cuff 60, but not at cuff 61. Hence, strips 64A and 64B are inserted in the elastic 62 at one end and at the opposite end are inserted in the seam 71 with elastic 62 on the underside of cuff 61, holding the seam together.

Figures 5, 5A, 5B:
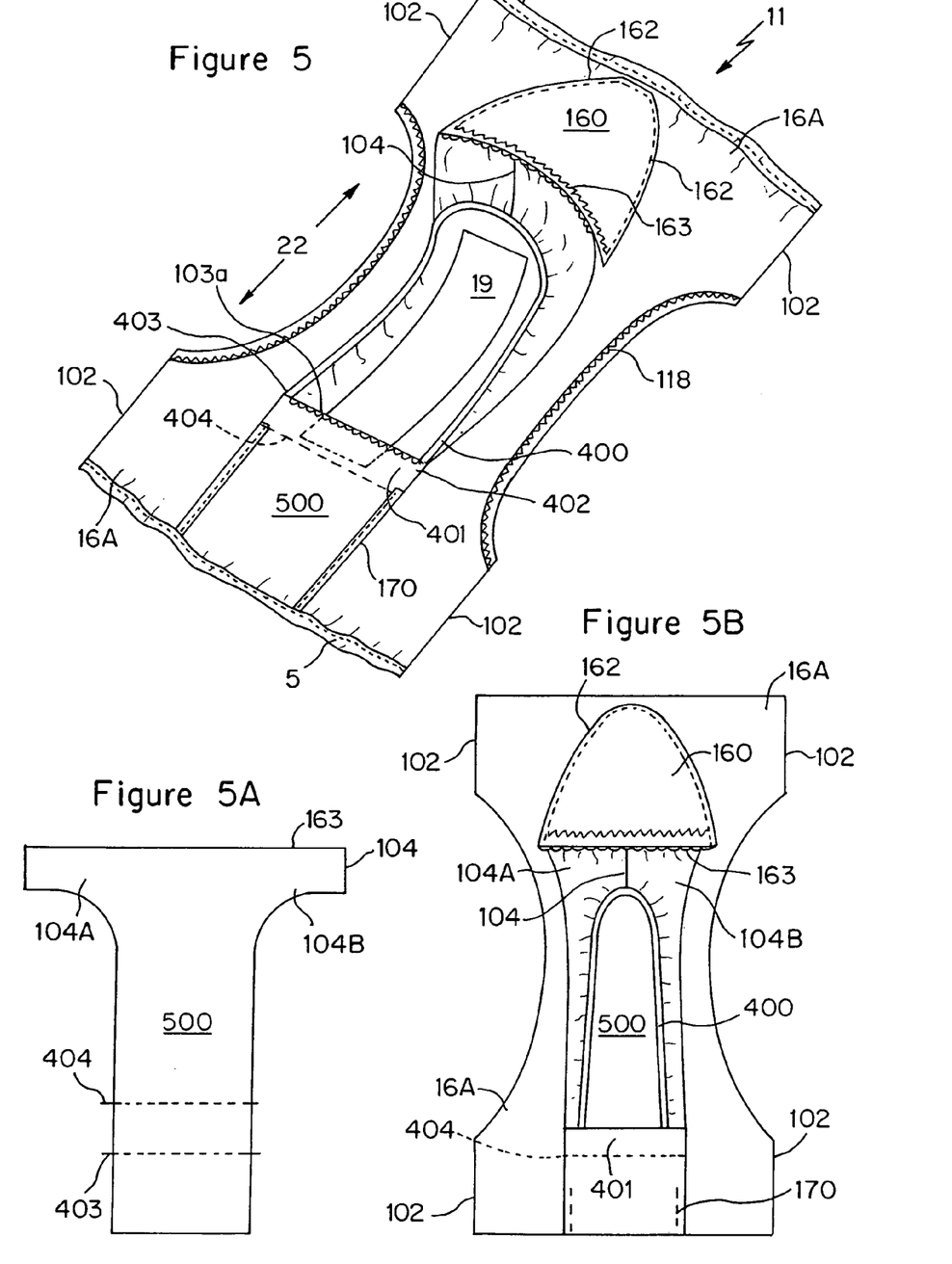
FIG. 5 depicts another embodiment of the invention, in which a lady's or man's underpant is fitted with a pocketed sling anchored by an anchor cuff.
FIG. 5A shows the pocket sling structure of FIG. 5.
FIG. 5B is a view of the cuffed anchor piece attached to an anchored pocket seamed and attached to the underlying pant as an anchor cloth.

In another embodiment, depicted in FIG. 5, the (anchor) liner cloth 16 of the previously described embodiments now becomes 16A the outermost surface of protective underwear diaper 11 in that it establishes conventional underwear, shown opened at side seams 102. This, for example, could be a lady's panty (or a man's Jockey® pant) by simply closing seams 102. However, what is important is not merely the outside appearance. With the waterproof or water-resistant shell being omitted, the same principles of the invention are applied to develop more aesthetic devices.

Still referring to FIG. 5, an anchor cuff 160 of triangular shape holds pocketed sling 500 in position to be worn. Pocketed sling 500 is of a waterproof or water-resistant material. Cuff piece 160 is stitched on the inside of the garment 11 at 162. This cuff is held to layer 16A, the garment or panty fabric 16A, in a triangular stitch pattern 162. At the widest end of the triangular cuff 160, pocketed sling 500 is attached at seam line 163 by an overlock finishing stitch. Leg hole 22 is covered by elastic 118. Elastic strip 5 finishes the outer edges of the garment 11.

In the rear portion of the garment, pocketed sling 500 is stabilized with stitching 170 on opposite sides of pocket 500. The resulting design is most advantageous for women who need a protective panty when in supine position.

The sidewalls of pocket sling 500 are brought together at seam 104. This process of forming the pocketed sling structure is best as seen in FIGS. 5A and 5B.

In FIG. 5A, the shape of pocket 500 is formed as sides 104A and 104B are bent inward and joined at seam 104. Elastic strip 400 is applied to fit the groin of the wearer as pocket 500 elasticizes around the pubic area. The opposite end of the pocket 500 is folded and stitched at lines 403 and 404, preferably covered by an elastic strip 403a that improves fit and water resistance. In FIG. 5B, the cuff 160 is joined to the end of pocket 500, at overlock stitch line 162. Folded walls 104A and 104B are seamed at 104, creating a top and under surface of the pocket now both held together by overlock stitching 163. Pocket 401 of FIG. 5 established under and longitudinally displaced from stitches 403, 404 retains one end of an optional absorbent pad 19, as shown. The opposite end of the pad is retained by the pocket 500 at cuff 160. The panty will be seamed at 102, and is now ready for application of elastic to the outer edge of the protective underwear.

Figures 6, 6A, 6B:
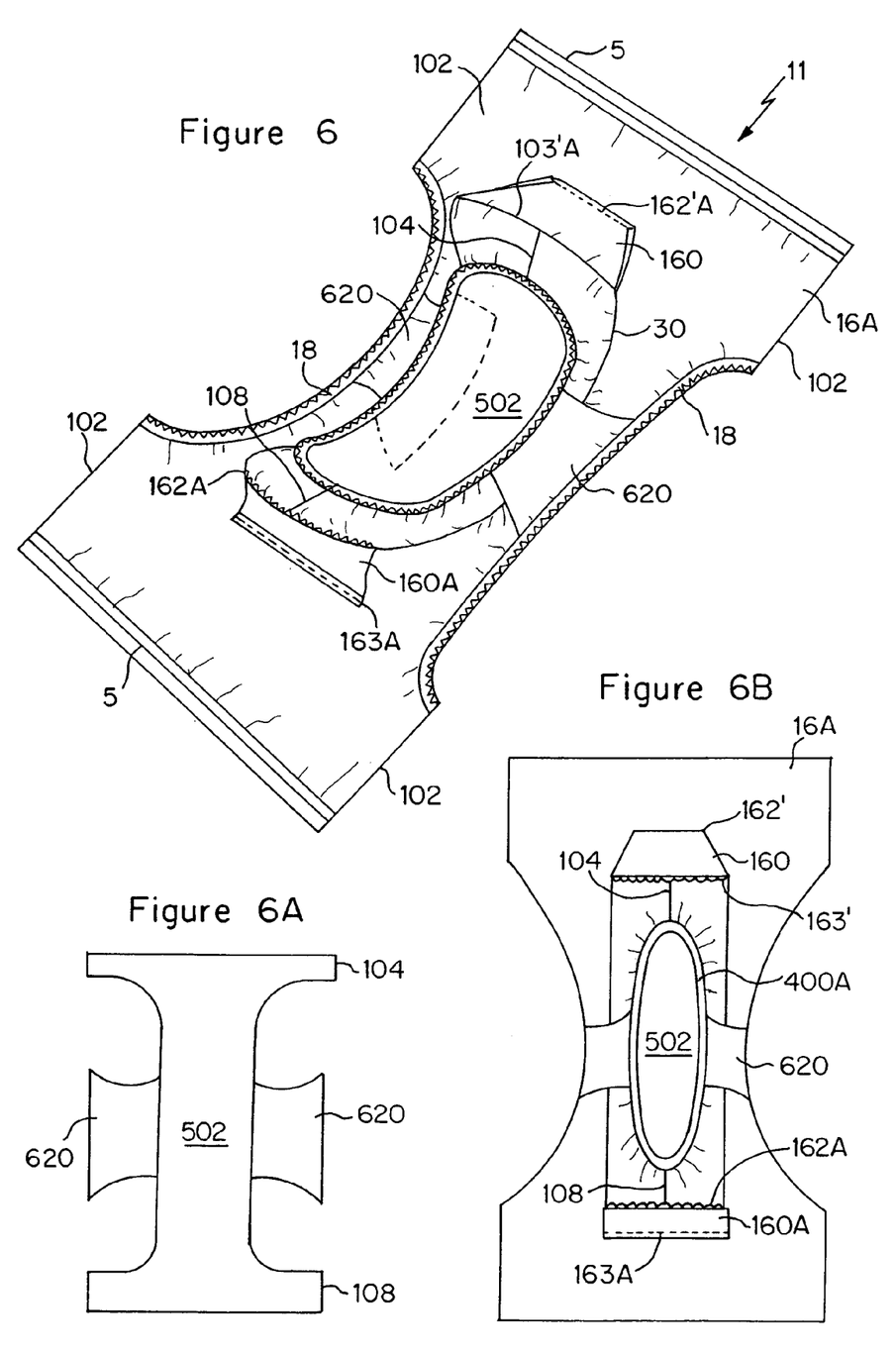
FIG. 6 is a view of another embodiment of ladies' or men's underpant, with a pocketed sling anchored by an anchor cuff in both frontal and rear portions of the garment.
FIG. 6A is a view of the pocketed sling structure of FIG. 6.
FIG. 6B shows the cuff anchor piece attached to an anchored pocket, attached to the underpant fabric as an anchor cloth.

FIG. 6, another embodiment of similar structure to FIG. 5, incorporates the same elements of structural formation; outermost surface layers 16A forming as both a panty and anchor cloth for a pocketed sling, the same elastic 5 for finishing outer waist portions of the garment, and side seams 102, that, when seamed form protective panty 11. The anchored pocket of FIG. 6 carries central connecting pieces 160 and 160A respectively at frontal and rear portions, now stitched centrally to 16A at stitch lines 162' and 163A. Anchor strips 620 are inserted in both sides of leg hole, elastic 18 at central portion of leg hole elastic 18 and then connected, or inserted in, elastic of pocket elastic 400A.

Manufacturing of garment strips 620 may be in reverse order of assembly by first being inserted in pocket elastic 400A and then attached to central portion of the panty (stitched over top of elastic 18). These connecting pieces 620 anchor the pocket 502 without piercing the fluid absorbing or containing area of pocket 502. The connecting pieces suspend the pocket 502 centrally at opposite ends. The pocket 502 is connected at opposite ends by seams 104 and 108. Elastic 18 finishes the leg hole. Elastic 400A terminates within seam 104, and the outermost edges of the pocket is finished by overlock stitch 163' and 162A.

In FIG. 6A, pocket 502 shows side anchor strips 620 prior to attachment to layer 16A per FIG. 6B.

In FIG. 6B, center anchor strips 620 are now encased in elastic 400A by stitching.

Figure 7:
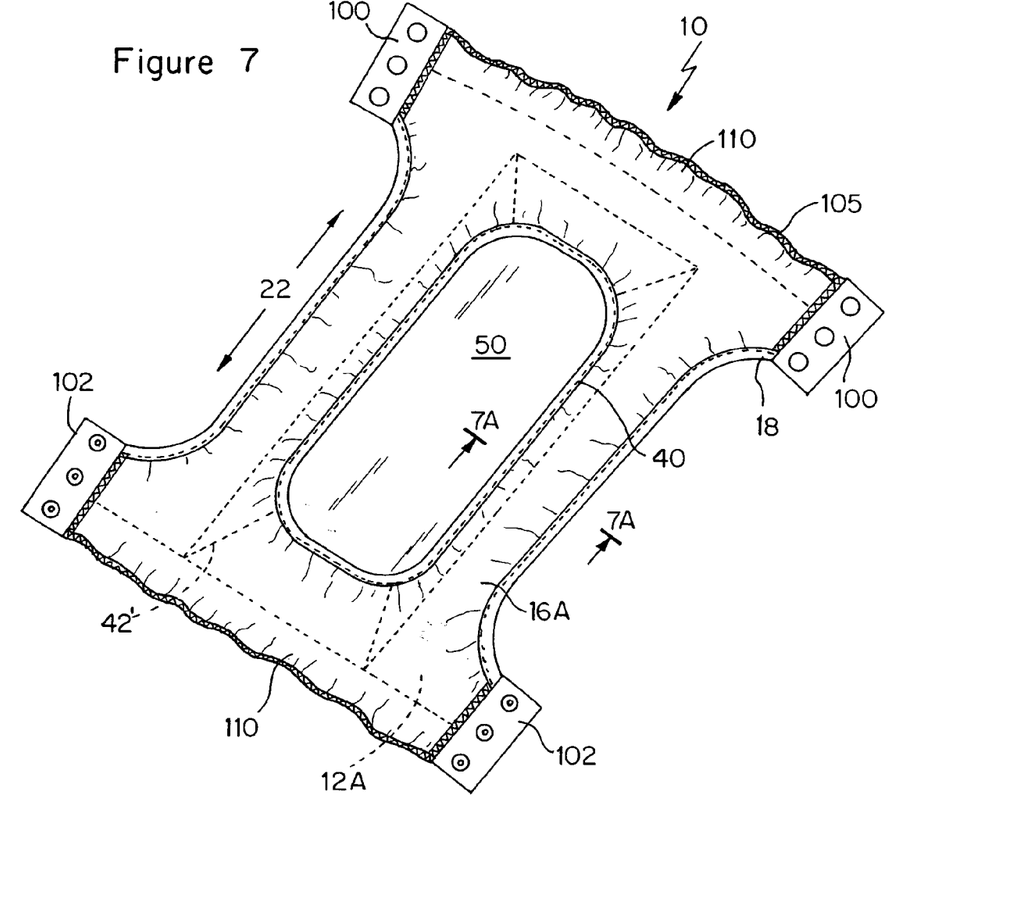
FIG. 7 is a plan view of an embodiment of a reusable diaper having snaps, with a submerged pocket sling produced in accordance with the principles of the invention, and opened in position to be worn, and with cutaway to expose an underlying shell.

In FIG. 7, there is yet another embodiment of an anchored pocket sling. This embodiment 100 is identical to FIG. 1 with the exception that the pocketed structure is attached, suspended below the anchor cloth; therefore, the pocket 50 resides between the shell 12 and anchor cloth 16.

FIG. 7 also depicts side snap fasteners or strips 100, 102 for fastening sides of garment together for wearing. Side snap fasteners strips 100, 102 are used in this garment as an alternative to Velcro® fasteners shown in earlier figures.

Waist elastic 110 is also positioned beneath anchor cloth 16A, so as to protect the skin of a wearer in the event that the elastic may be wide and need fabric over it. Overlock stitching 105 connects 16A with outer shell 12 at the outermost edge of the garment.

On the underside, dotted lines represent the now suspended and floating pocket, 50, of same structure as pocket 50 of FIG. 1. It is a hidden pocket, suspend by the joining of perimeter edge of material 13 to anchor cloth 16A at elastic 40. Seam lines 42 are joined as in FIG. 1, but no stitch line 17 is necessary in this embodiment as the base of the pocket floats. This feature further enhances the waterproof property of the pocket.

Figure 7A:
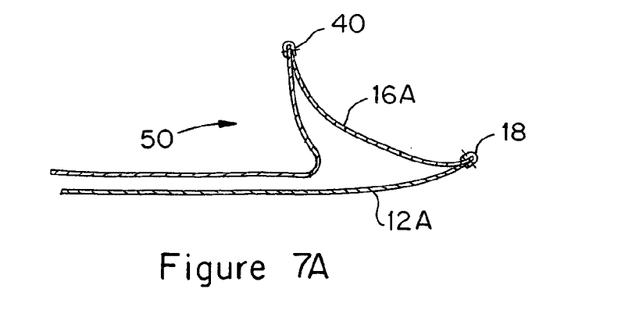
FIG. 7A is a cross-sectional view of a diaper taken along line 7A—7A of FIG. 7.

In FIG. 7A, pocket 50 is suspended between anchor cloth 16A and shell 12A. Elastic 40 holds the edges of the pocket and anchor cloth.

Figure 7B:
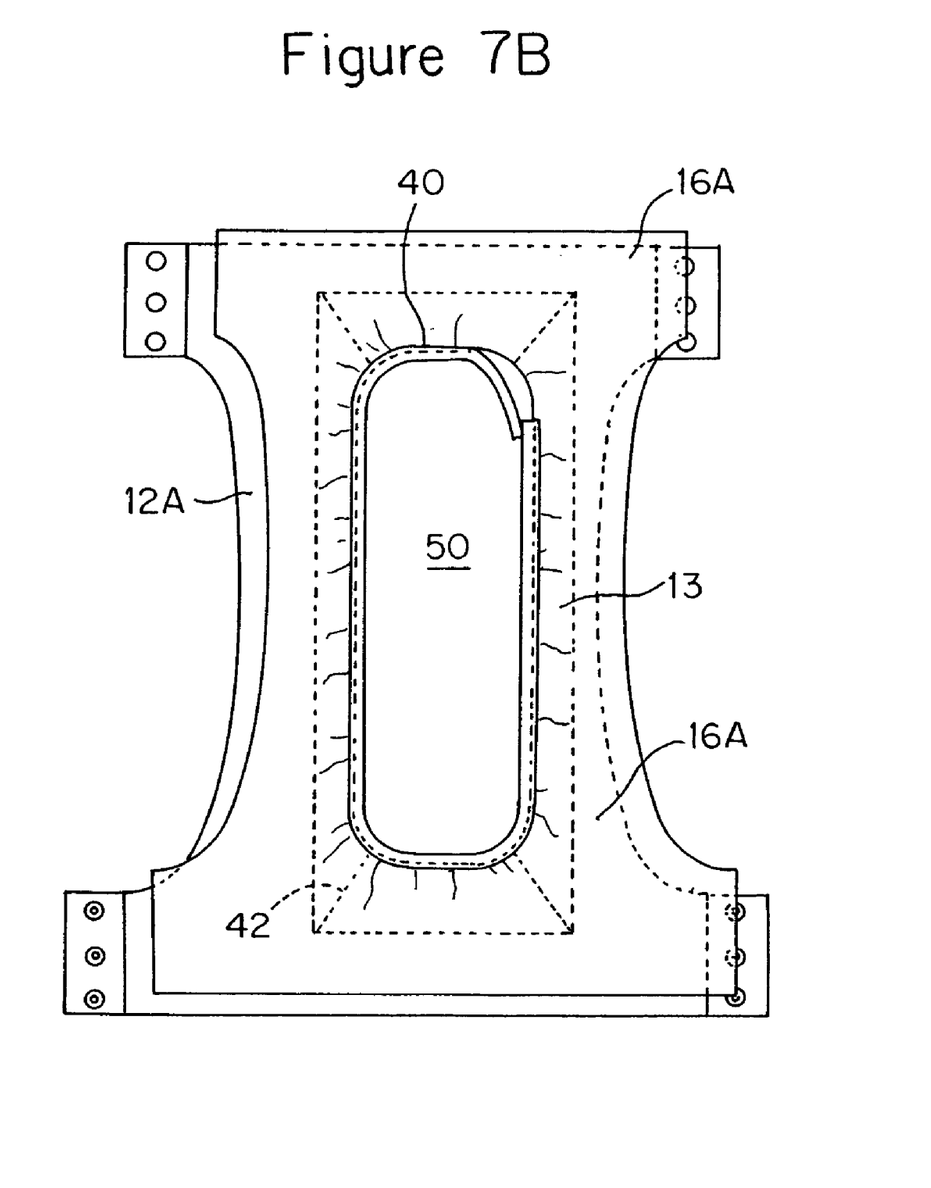
FIG. 7B shows an anchor cloth holding the submerged pocket, with the pocket attached on the underside of the anchor cloth and overlying a shell cloth with snap fasteners.

In FIG. 7B, another view of the manufacture of the submerged pocked design, anchor cloth 16A overlies shell 12A.

Figure 8:
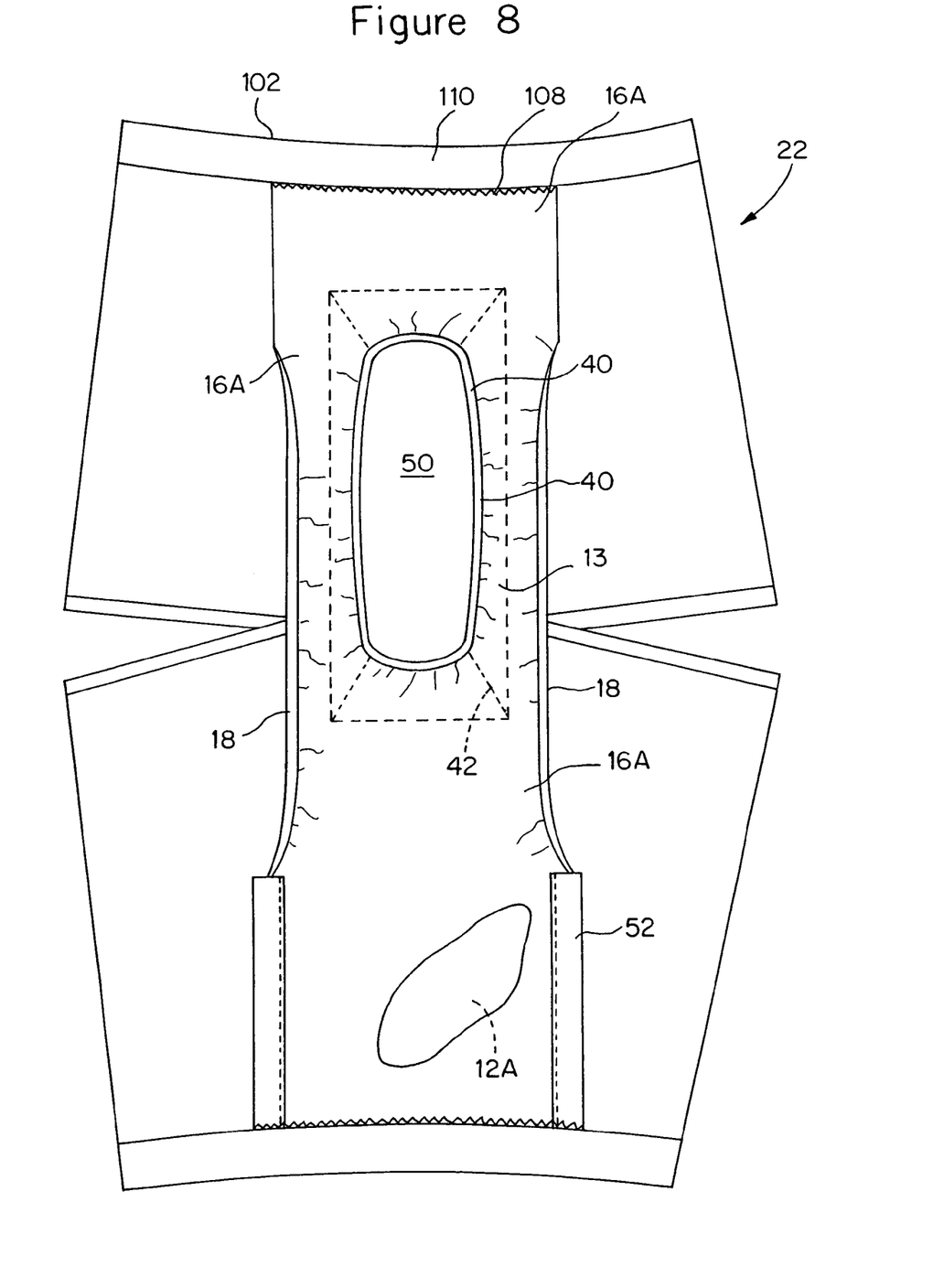
FIG. 8 is a plan view of another embodiment of a man's boxer underpant, open at its side seams, laid flat with a submerged pocket-sling structure retrofitted and produced in accordance with the principles of the invention.

In FIG. 8 the submerged pocket structure of FIG. 7 is applied to a male boxer short 22. The submerged pocket 50 includes the principles of the invention disclosed in FIG. 6 including submerged pocket 50, with seam lines 42, suspended between anchor cloth 16A and waterproof piece 12A held on opposite sides by elastic 18. The addition to this variation of the invention is anchor strip 52 which stabilizes the protective sling in the rear portion of boxer short 22.

Boxer short 22 has an elastic waist 110 and a sling device with submerged pocket 50 held to central frontal interior portion of boxer pant 22 at stitching 118.

Figure 9:
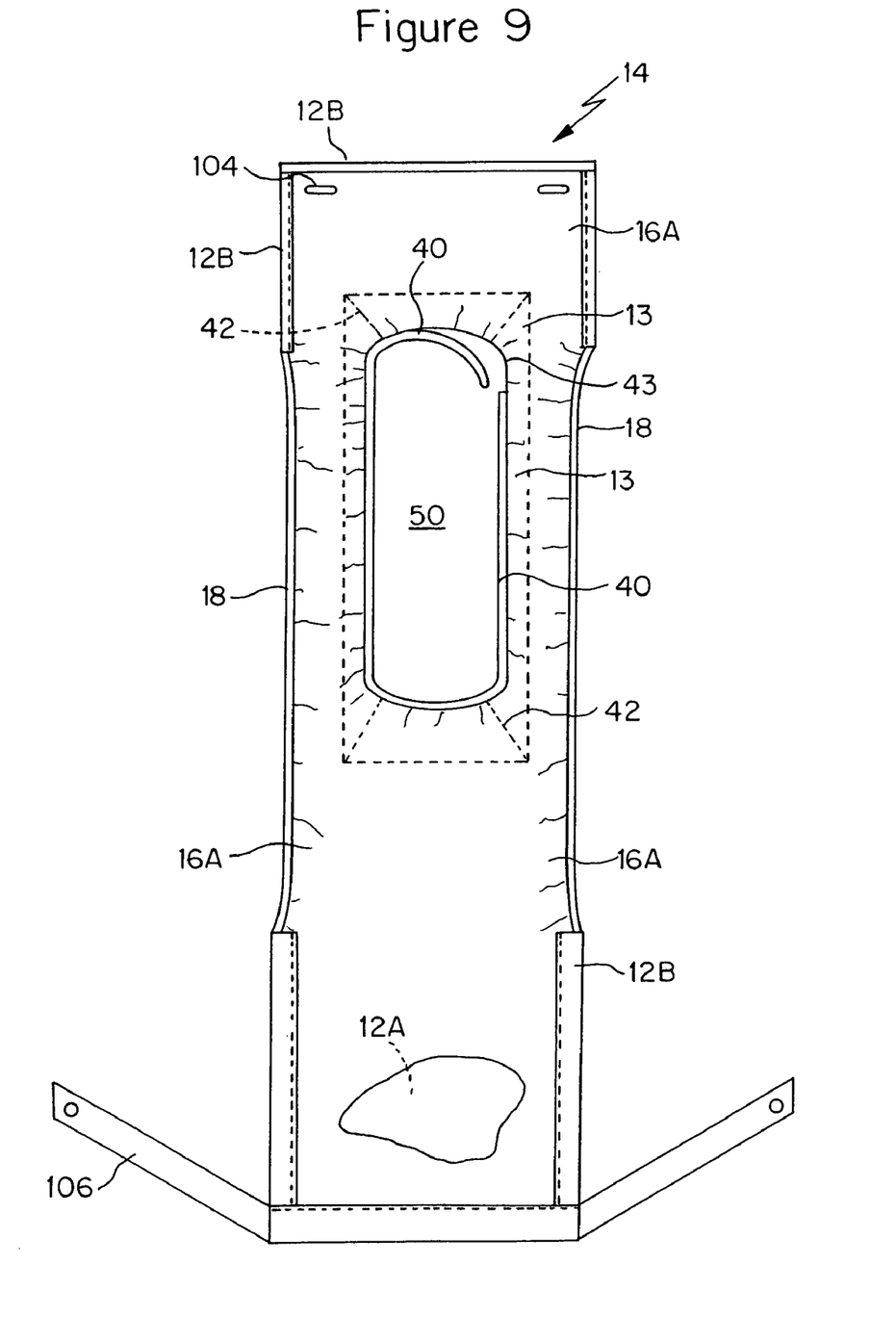
FIG. 9 is plan view of a belted undergarment with submerged pocket, produced per this invention, with cutout to expose an underlying shell.

In FIG. 9, the submerged pocket of FIGS. 6, 7 and 8 is the same except, as shown, as a belted undergarment 14, where all principles of the invention are applied, and for fastening to the wearer, belt 106 with button 114 is coupled with buttonhole 104. Buttonhole 104 pierces with stitching both shell 12A and anchor cloth 16A. Folded edge 12B finishes the ends of the undergarment.

What is claimed is:

1. A protective undergarment, comprising:
   an outer layer of fluid-resistant material shaped to conform to a buttock and leg region of a user;
   an anchor layer of fluid absorbent material secured to the outer layer and having a shape generally conforming to that of the outer layer; and
   an inner layer of fluid-resistant material with four sides which sides are stitched directly to the anchor layer but not directly to the outer layer, the stitched four sides thereof being displaced inwardly from corresponding sides toward a center of the anchor layer, and the inner layer at all four sides thereof extending from where stitched to the anchor layer to respective free edges on the inner side of the undergarment when the undergarment is worn, to form a pocket.

2. The protective undergarment as in claim 1, wherein a base portion of the pocket is positioned on a surface of the anchor layer.

3. The protective undergarment as in claim 1, wherein the inner layer is initially a rectangular piece of material, wherein triangular portions near the corners of the pocket are removed, and remaining adjacent sides together to form said pocket, an outer edge of the pocket being covered by an elastic strip.

4. The protective undergarment as in claim 1, wherein the sides are interconnected to form the pocket.

5. The protective undergarment as in claim 4, wherein the sides are interconnected by stitching.

6. The protective undergarment as in claim 4, wherein adjacent sides of the inner layer intersect at stitch lines to form corners of the pocket.

7. The protective undergarment as in claim 1, wherein the respective free edges of all said four sides the inner layer are circumscribed by an elastic strip.

8. The protective undergarment as in claim 1, wherein the anchor layer is secured to the outer layer only at a peripheral edge of the outer layer.

\* \* \* \* \*